United States Patent [19]
Jarvik

[11] Patent Number: 5,824,070
[45] Date of Patent: Oct. 20, 1998

[54] HYBRID FLOW BLOOD PUMP

[76] Inventor: Robert Jarvik, 124 W. 60 St., New York, N.Y. 10023

[21] Appl. No.: 544,989

[22] Filed: Oct. 30, 1995

[51] Int. Cl.[6] .................................................... A61M 1/12
[52] U.S. Cl. ................................. 623/3; 600/16; 604/131
[58] Field of Search ............................... 623/3; 604/151; 417/353; 415/900; 600/16, 17

[56] References Cited

U.S. PATENT DOCUMENTS

| | | | |
|---|---|---|---|
| 3,647,324 | 3/1972 | Rafferty et al. | 417/420 |
| 4,135,253 | 1/1979 | Reich et al. | 3/1.7 |
| 4,589,822 | 5/1986 | Clausen et al. | 415/170 A |
| 4,625,712 | 12/1986 | Wampler | 128/1 D |
| 4,688,998 | 8/1987 | Olsen et al. | 417/356 |
| 4,704,121 | 11/1987 | Moise | 623/3 |
| 4,817,586 | 4/1989 | Wampler | 415/900 X |
| 4,994,078 | 2/1991 | Jarvik | 623/3 |
| 5,145,333 | 9/1992 | Smith | 415/900 X |
| 5,178,515 | 1/1993 | Tsuchiya et al. | 415/900 X |
| 5,275,580 | 1/1994 | Yamazaki | 623/3 X |
| 5,370,509 | 12/1994 | Golding et al. | 417/423.1 |
| 5,376,114 | 12/1994 | Jarvik | 623/3 |
| 5,441,535 | 8/1995 | Takahashi et al. | 623/3 |
| 5,443,509 | 8/1995 | Yamane | 623/3 |
| 5,507,629 | 4/1996 | Jarvik | 623/3 |
| 5,588,812 | 12/1996 | Taylor et al. | 415/900 X |

*Primary Examiner*—John D. Yasko

[57] ABSTRACT

A novel hydrodynamic blood pump with a very clean flow path free of outflow stator blades which have been found to be a site of blood clot formation is introduced. The invention combines an axial flow pump impeller with a bladeless volute structure typical of centrifugal pumps to obtain a miniaturized hybrid blood pump configured to be surgically implanted such that the axial flow pump impeller is located within the heart and the spiral volute portion of the device is located outside the heart.

6 Claims, 2 Drawing Sheets

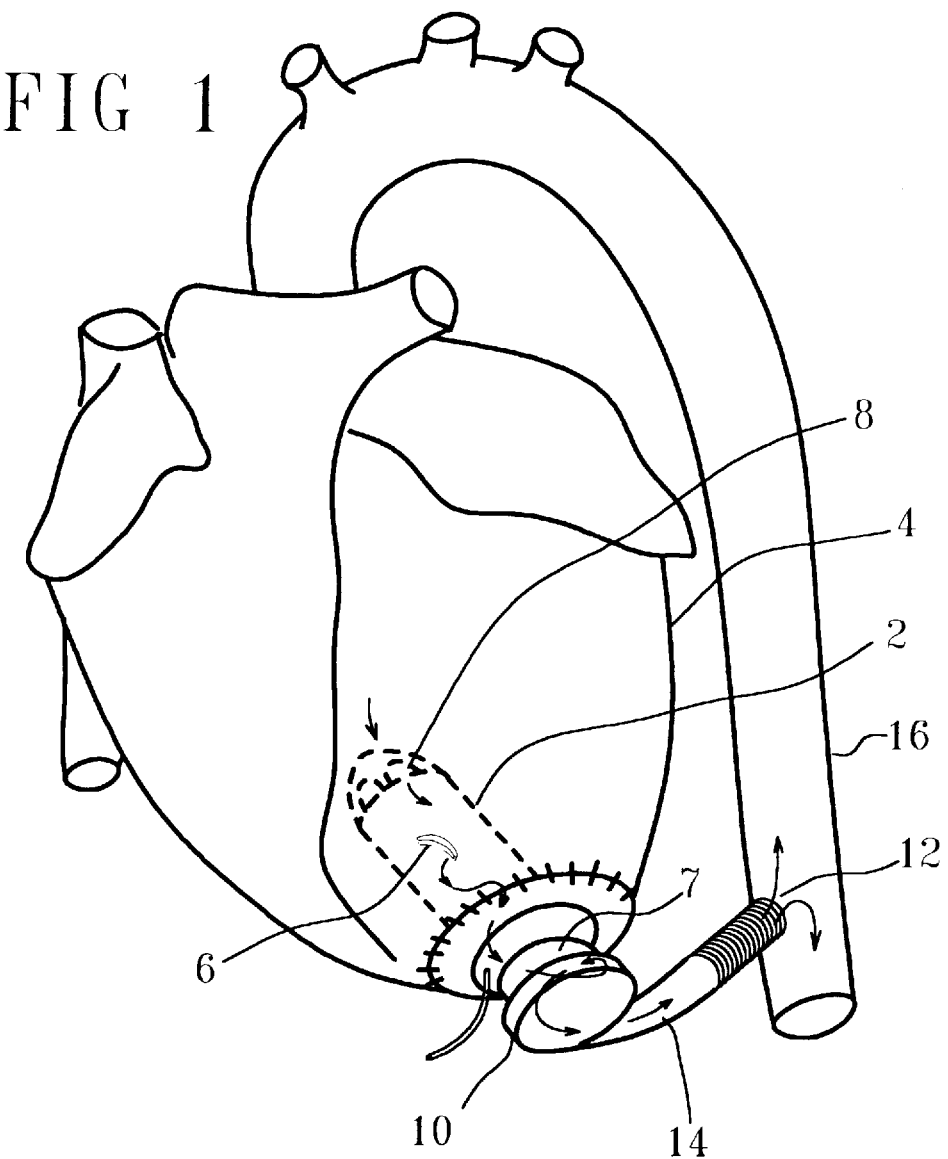

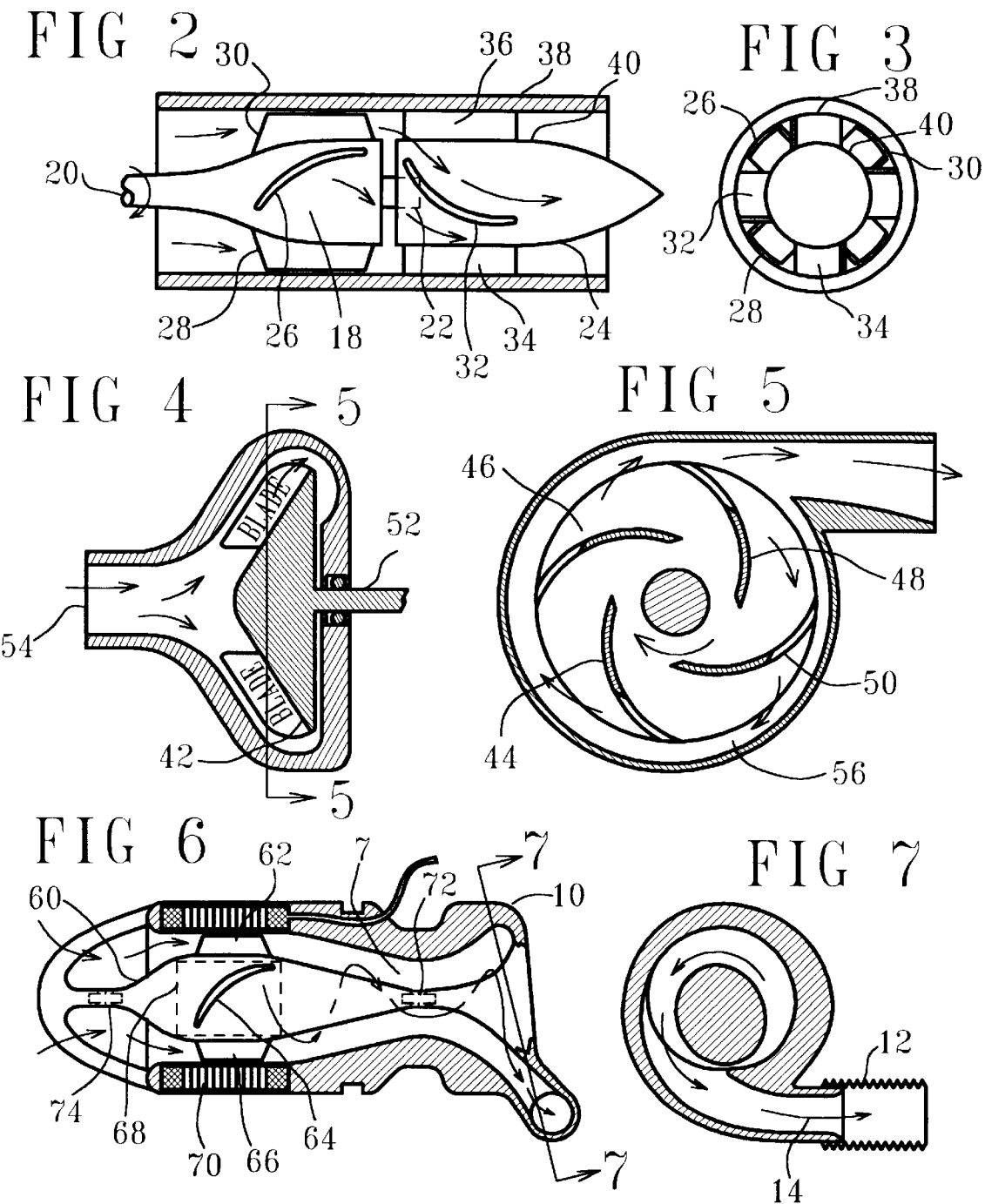

HYBRID FLOW BLOOD PUMP

BACKGROUND

Rotary blood pumps are becoming widely applied in medical applications and have proven capable of sustaining experimental animals for periods as long as six months. Problems of blood damage and seizure of rotary impellers have been overcome in some devices, which holds promise for their successful application as permanent artificial hearts. However, anticoagulation is required to prevent blood clots from obstructing the flow channels of the pumps, and in the event of infection there is more likelihood of clots occurring in any crevices or stagnant areas within the device. Axial flow pumps (also known as propeller pumps) generally operate at higher speeds than centrifugal flow pumps for a given flow and pressure, and therefore are smaller, have lower surface area, and can be powered by smaller electric motors. However, a disadvantage of axial flow pumps is that they require outflow stators to operate efficiently. The outflow stator blades protrude into the flow channel and provide sites including crevices where blood clots can adhere and obstruct the flow. Centrifugal pumps generally utilize a volute rather than the stator blades incorporated in axial pumps to convert the rotary fluid momentum imparted by the impeller into pressure energy at the outflow. The centrifugal pump volute provides a very clean outflow channel which may be seamless and highly polished to remain free of thrombus. The present invention combines an axial flow impeller with a centrifugal volute and thereby eliminates the outflow stators while retaining acceptable efficiency. This hybrid principle when used with proper hydraulic geometric flow channel design provides optimal blood washing of the pump outflow. Anticoagulation can be minimized or eliminated, and the device is less susceptible to thrombus formation in the event of systemic infection.

OBJECTS OF THE INVENTION

An object of the invention is to provide a miniature blood pump to function as an artificial heart which will remain unobstructed by thrombus for many years.

A further object of the invention is to provide a bladeless outflow channel for a blood pump utilizing an axial flow impeller, or a mixed flow impeller running within a generally cylindrical chamber.

Another object of the invention is to increase the hydraulic efficiency of an axial flow pump having no outflow stator blades.

A still further object of the invention is to minimize or eliminate the need for anticoagulation in patients sustained with rotary artificial hearts.

These, and additional objects of the invention will be more fully understood by referring to the drawings and specific descriptions in the following sections.

THE DRAWINGS

FIG. 1 is a schematic drawing of a natural heart with an intraventricular blood pump of the present invention implanted within it.

FIG. 2 is an illustration of an axial flow pump impeller and stator set shown within a longitudinally sectioned cylindrical housing.

FIG. 3 is an end view of the pump of FIG. 2 shown looking into the pump outflow.

FIG. 4 is a longitudinal sectional view of a centrifugal pump.

FIG. 5 is a cross sectional view of the centrifugal pump of FIG. 4 at section 5—5.

FIG. 6 is a longitudinal view of a hybrid blood pump in which the housing is shown in section and the rotor and bearing support members within it are shown not in section.

FIG. 7 is a cross sectional view of the pump of FIG. 6 taken along the section plane 7—7.

SPECIFIC DESCRIPTION OF THE PREFERRED EMBODIMENT

FIG. 1 illustrates a hybrid blood pump 2 implanted in the apex of the left ventricle 4 for permanent cardiac support. The position of one axial flow pump blade 6 is shown to illustrate that its action on the bloodstream is to change the direction of the flow which enters the pump axially (arrow 8) to a significantly rotational and circumferential direction, so that the blood leaves the impeller with a spiral motion as shown by additional arrows in FIG. 1 and as more clearly illustrated by the arrows of FIG. 6. After the impeller creates the swirling motion of the bloodstream by imparting rotational momentum to the fluid, the flow passes through a conduit section of the pump 7 and encounters the volute section of the pump 10 which converts this rotary momentum into pressure energy. As the blood passes into the outflow graft 12 it now flows longitudinally through the graft with little swirl as illustrated by arrow 14. This arrangement has the advantage that the direction of the flow entering from the ventricle is also turned approximately 90 degrees which anatomically directs it properly for connection of the graft 12 to the aorta 16.

FIG. 2 illustrates the typical components of an axial or mixed flow pump which utilizes outflow stators. The impeller 18 is driven by a shaft 20 which may be supported by a bearing 22 mounted within the stationary hub 24 of the outflow stator portion of the pump. Impeller blades 26, 28 and 30 mounted on hub 18 impart rotary momentum to the fluid as they pump it. The hub may be un-tapered in a strictly axial design, or may include some taper, as illustrated in FIG. 2, in which case it is a mixed flow impeller (mixed flow refers to the fact that the flow across the impeller is partially axial and partly radial). Pumps utilizing an impeller that turns within a generally cylindrical housing in which the flow leaving the impeller is fundamentally axial rather than partly radial are referred to as propeller pumps even if the hub is tapered. The stator blades, 32, 34, and 36 change the direction of the flow from the rotational direction to the axial direction as illustrated by the arrows, and in doing so convert the rotational fluid momentum energy into pressure energy at the pump outlet. Without outflow stator blades the pump would be very inefficient, and a great deal of energy would be lost in the swirling fluid stream. However, the outflow stator blades present a problem in blood pump designs, because they must join the pump housing at their outside diameter 38, which creates an unavoidable crevice, even if a fillet is used. Where the blades join the hub 40, an additional crevice exists. These are sites where thrombus accumulation can occur and from which thrombus accumulation can develop severe enough to obstruct the flow. Additionally, if the flow is pulsatile, as it will be in most applications, the flow across the stator blades may be unsteady and may separate, further aggravating the problem of thrombus accumulation around the stator blades.

FIG. 3 shows a four-bladed stator set which presents sixteen crevices at the junctions of both sides of each blade with both the housing and the hub. Elimination of these crevices is one of the advantages of the hybrid pump of the present invention.

FIGS. 4 and 5 illustrate a typical centrifugal pump impeller with blades 44, 46, 48, and 50. The impeller is driven by shaft 52 and converts the axial flow stream entering the inflow port into a circumferential flow stream at the outside diameter of the impeller. As the fluid progresses through the pump blade section, it obtains rotational momentum due to the action of the impeller. The fluid encounters the outflow tube 58 which is affixed tangentially to the pump housing and is typically referred to as the pump discharge. A simple tapered tangential tube may be used, or the outside wall of the pump housing may be shaped as a spiral volute to more efficiently recover the momentum of the fluid as it enters the discharge portion of the pump. This represents the simple basic structure of the centrifugal pump volute and discharge, which is often a bladeless structure with no crevices.

FIG. 6 illustrates the preferred embodiment of the hybrid blood pump of the present invention. The pump 60 has the impeller blades 62, 64, and 66 mounted on it, but there are no stator blades used. In this design the rotor also has the magnet 68 (dotted lines) of a brushless DC motor 70 and is mounted on blood-immersed bearings 72, 74 at both ends. Fully or partially magnetically suspended pump impellers may also be used without departing from the principle of the invention. The arrows illustrate the spiral path the blood flow follows after the impeller imparts rotational momentum to it. FIG. 7 is a sectional view through the outflow section of the pump (note that this section is slanted with reference to the axis of rotation of the impeller), which is formed with a volute generally configured as commonly used with centrifugal pumps. The exact design of the volute portion of the pump may be geometrically optimized utilizing advanced computational fluid mechanics to yield high hydrodynamic efficiency and avoid any areas of flow separation. Thus, the combination of the axial or mixed flow impeller with the centrifugal volute provides a superior blood pump free of outflow stator related sites where thrombus may form. The simple structure also permits wide flow channels which may be highly polished to further prevent thrombus formation.

The information disclosed in the description of the present invention is intended to be representative of the principles that I have described. It will thus be seen that the objects of the invention set forth above and those made apparent from the preceding description are efficiently obtained and that certain changes may be made in the above articles and constructions without departing from the scope of the invention. It is intended that all matter contained in the above description or shown in the accompanying drawings shall be interpreted as illustrative but not in a limiting sense. It is also understood that the following claims are intended to cover all of the generic and specific features of the invention herein described and all statements of the scope of the invention which as a matter of language might be said to fall there between.

I claim:
1. A blood pump comprising,
   a. hydrodynamic pump impeller means, contained within a generally cylindrical chamber having an inflow and an outflow opening, said impeller means supported by bearing means and driven by power means,
   b. means for receiving blood from said inflow opening in an axial direction, impart rotational momentum to the blood, and eject said blood in a substantially axial direction through said outflow opening, and,
   c. volute means comprising,
      1. a chamber downstream of said outflow opening into which blood enters axially with rotational as well as axial fluid momentum and within which the flow channel is expanded radially, and
      2. generally tangential discharge means.
2. The blood pump of claim 1 in which said chamber includes a radially spiraling outer wall blended tangentially into said tangential discharge means.
3. The blood pump of claim 1 in which said chamber means include spirally shaped outer walls which impart a spiral flow path to the blood passing therethrough.
4. A hybrid blood pump constructed with no outflow stators comprising impeller means of the propeller pump type combined with volute means of the centrifugal pump type.
5. The blood pump of claim 4 in which said chamber and discharge means are shaped so that blood passing therethrough takes a flow path which spirals in both the axial as well as the radial directions.
6. A ventricular assist device comprising:
   a. electric motor means enclosed within housing means adapted to be surgically implanted within a chamber of the heart,
   b. axial flow pump impeller means adapted to be implanted within the heart, mounted upon rotor means rotated by said motor means,
   c. pump volute and discharge means, and
   d. conduit means adapted to extend across a wall of the heart and positioned between said impeller means and said pump volute means.

* * * * *